United States Patent [19]

Cheng et al.

[11] Patent Number: 5,834,502
[45] Date of Patent: Nov. 10, 1998

[54] TRIAZOLYLMETHYL-INDOLE ETHYLAMINE BISULFATE SALT

[75] Inventors: Chen Y. Cheng, Edison; James A. McCauley, Belle Mead; Jennifer L. Vandrilla, Edison; Thomas R. Verhoeven, Cranford; Robert D. Larsen, Bridgewater, all of N.J.

[73] Assignee: Merck & Co., Inc., Rahway, N.J.

[21] Appl. No.: 682,815

[22] Filed: Jul. 11, 1996

Related U.S. Application Data

[60] Provisional application No. 60/001,055, Jul. 11, 1995.
[51] Int. Cl.[6] .................. A61K 31/41; C07D 403/06
[52] U.S. Cl. ......................... 514/383; 548/266.4
[58] Field of Search ................... 514/383; 548/266.4

[56] References Cited

U.S. PATENT DOCUMENTS 5,298,520  3/1994  Baker et al. ........................ 514/383
5,527,817  6/1996  Baker et al. ........................ 514/383

FOREIGN PATENT DOCUMENTS

| | | |
|---|---|---|
| 0 497 512 A2 | 8/1992 | European Pat. Off. . |
| 0 573 221 A1 | 12/1993 | European Pat. Off. . |
| WO93/25547 | 12/1993 | WIPO . |
| WO 95/32197 | 11/1995 | WIPO . |

OTHER PUBLICATIONS

Martin et al. "Analysis of the 5–HT receptor, etc." Arch. Pharmacol (1990) pp. 111–119, 342.

*Primary Examiner*—Patricia L. Morris
*Attorney, Agent, or Firm*—Melvin Winokur

[57] ABSTRACT

The bisulfate salt of N,N-dimethyl-2-[5-(1,2,4-triazol-1-ylmethyl)-1H-indol-3-yl]ethylamine is a selective agonist of 5-$HT_1$-like receptors and is useful in the treatment of migraine and associated disorders.

17 Claims, 2 Drawing Sheets

TRIAZOLYLMETHYL-INDOLE ETHYLAMINE BISULFATE SALT

The instant case is a national filing under 35 U.S.C. § 111, claiming priority under 35 U.S.C. § 119(e), of provisional application No. 60/001055, filed Jul. 11, 1995, still pending.

FIELD OF THE INVENTION

The present invention relates to a particular salt of a pharmaceutically active agent. More particularly, the invention relates to a bisulfate salt of a substituted triazolylmethyl-indole ethylamine derivative, i.e., N,N-dimethyl-2-[5-(1,2,4-triazol-1-ylmethyl)-1H-indol-3-yl]ethylamine, which acts on 5-hydroxytryptamine (5-HT) receptors, being a selective agonist of so-called "5-HT$_1$-like" receptors. This compound is therefore useful in the treatment of migraine and associated disorders, conditions for which a selective agonist of these receptors is indicated.

BACKGROUND OF THE INVENTION

5-HT$_1$-like receptor agonists which exhibit selective vasoconstrictor activity have been described as being of use in the treatment of migraine (see, for example, A. Doenicke et al., The Lancet, 1988, Vol. 1, 1309–11).

U.S. Pat. No. 5,298,520, which issued on Mar. 29, 1994 and is assigned to Merck Sharp & Dohme Limited, describes a class of substituted imidazole, triazole and tetrazole derivatives which are selective agonists of 5-HT$_1$-like receptors and are useful in the treatment of migraine and associated conditions. Pharmaceutically acceptable salts of N,N-dimethyl-2-[5-(1,2,4-triazol-1-ylmethyl)-1H-indol-3-yl]ethylamine are generically encompassed within the scope of U.S. Pat. No. 5,298,520, in which the oxalate-hemihydrate, succinate and benzoate salts are specifically disclosed. WO 93/25,547, published on Dec. 23, 1993, and assigned to Merck Sharp & Dohme Limited, describes a hemisulfate salt of N,N-dimethyl-2-[5-(1,2,4-triazol-1-ylmethyl)-1H-indol-3-yl]ethylamine and its use in antimigraine therapy.

However, there is no specific disclosure in the above references of the newly discovered crystalline bisulfate salt of structural Formula I below.

SUMMARY OF THE INVENTION

By this invention there is provided a new crystalline bisulfate salt of N,N-dimethyl-2-[5-(1,2,4-triazol-1-ylmethyl)-1H-indol-3-yl]ethylamine. Specifically, the invention provides crystalline N,N-dimethyl-2-[5-(1,2,4-triazol-1-ylmethyl)-1H-indol-3-yl]ethylamine bisulfate salt (1:1) of the following structural Formula I:

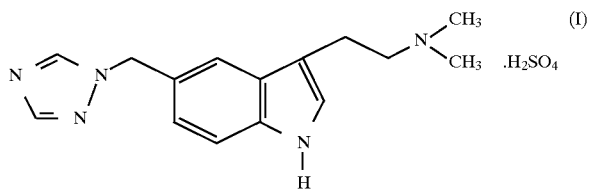

and pharmaceutically acceptable solvates, including hydrates, thereof.

More specifically this salt is comprised of one molar equivalent of mono-protonated N,N-dimethyl-2-[5-(1,2,4-triazol-1-ylmethyl)-1H-indol-3-yl]ethylamine cation and one molar equivalent of bisulfate anion.

The bisulfate salt of the present invention, which exhibits selective 5-HT$_1$-like receptor agonist activity, is particularly useful in the treatment of migraine and associated conditions, e.g., cluster headache, chronic paroxysmal hemicrania, headache associated with vascular disorders, tension headache and pediatric migraine.

BRIEF DESCRIPTION OF THE INVENTION AND PREFERRED EMBODIMENTS

Figure 1:
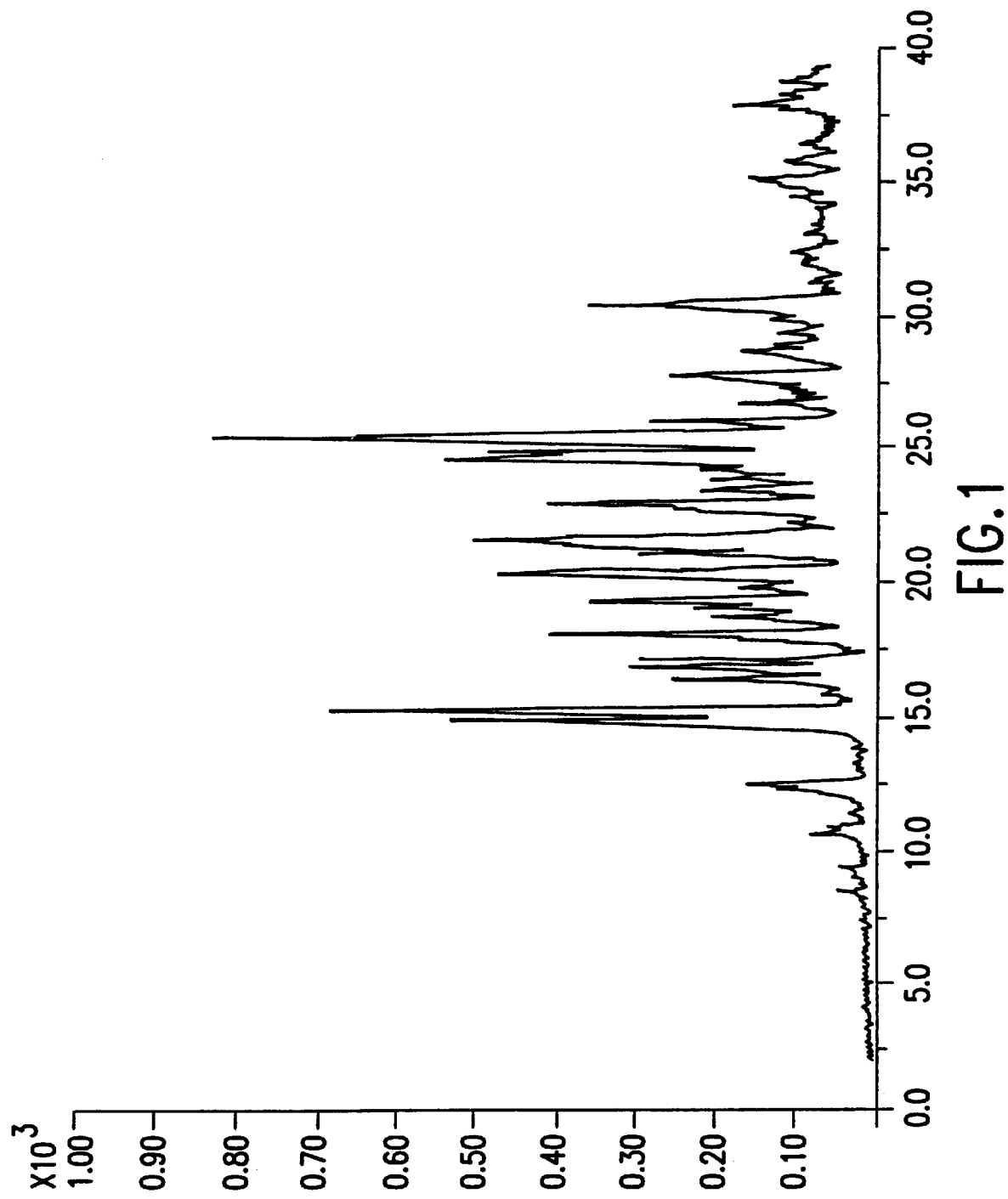
FIG. 1 is a characteristic X-ray diffraction pattern of the crystalline bisulfate compound of Formula I.

The present invention provides a pharmaceutical composition comprising the crystalline bisulfate salt of Formula I above, or a pharmaceutically acceptable solvate thereof, in association with one or more pharmaceutically acceptable carriers.

The compositions in accordance with the invention are suitably in unit dosage forms such as tablets, pills, capsules, powders, granules, sterile solutions or suspensions, metered aerosol or liquid sprays, drops, ampoules, auto-injector devices or suppositories; for oral, parenteral, intranasal, sublingual or rectal administration, or for administration by inhalation or insufflation. Formulation of the compositions according to the invention can conveniently be effected by methods known from the art, for example as described in Remington's Pharmaceutical Sciences, 17th Ed., 1995.

For example, for preparing solid compositions such as tablets, the active ingredient is mixed with a pharmaceutical carrier, e.g., conventional tableting ingredients such as microcrystalline cellulose, corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of the salt of Formula I above. When referring to these preformulation compositions as homogeneous, it is meant that the active ingredient is dispersed uniformly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention.

The liquid forms in which the salt of the present invention may be incorporated for administration orally, intranasally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of migraine, a suitable dosage level is about 0.01 to 250 mg/kg per day, preferably about 0.05 to 100 mg/kg per day, and especially about 0.05 to 5 mg/kg per day. The compositions may be administered on a regimen of 1 to 4 times per day.

In one embodiment of the composition according to the present invention is provided a pharmaceutical composition in solid form adapted for sublingual administration, comprising the salt of Formula I as defined above or a pharmaceutically acceptable solvate thereof; one or more pharmaceutically acceptable buffering agents capable of imparting to the buccal cavity following administration a pH of at least 7.5; and one or more pharmaceutically acceptable excipients.

Oral compositions may be subject to certain drawbacks in the treatment of conditions such as migraine, because such conditions are often accompanied by nausea, which makes it difficult for a patient to tolerate an oral composition. Parenteral administration generally has the advantage of rapid absorption of drug, but this route of administration can be unacceptable to some patients, especially if the composition is presented in a form adapted for self-administration.

The salt of Formula I has in fact been found to possess a high solubility in water, rendering it especially amenable to the preparation of formulations, in particular intranasal formulations, which require relatively concentrated aqueous solutions of active ingredient. The solubility of the salt of Formula I in water, expressed in terms of the free base, has been found to be approximately 500 mg/ml. This can be compared with, for example, the solubility of the benzoate salt of N,N-dimethyl-2-[5-(1,2,4-triazol-1-ylmethyl)-1H-indol-3-yl]ethylamine (Example 18 of U.S. Pat. No. 5,298,520), which under comparable conditions has been found to be approximately 40 mg/ml.

Moreover, the bisulfate salt in accordance with the present invention is found to exhibit a low tonicity.

The practical consequence of the low tonicity of solutions of the salt according to the invention relative to the predicted value is realized in a consequential lowering of local irritancy in those regions of the body to which such solutions are administered. This effect is particularly notable in those regions possessing especially sensitive membranes, such as the intranasal cavity. Thus, in view of this property, combined with its high solubility as noted above, the bisulfate salt of Formula I is ideally suited to the preparation of aqueous intranasal formulations.

In a preferred embodiment of the composition according to the present invention, therefore, there is provided a pharmaceutical composition adapted for intranasal administration, which comprises the bisulfate salt of Formula I above or a pharmaceutically acceptable solvate thereof in association with one or more pharmaceutically acceptable carriers.

Intranasal formulations may generally be provided in liquid or dry powder forms. Satisfactory intranasal formulations must be sufficiently stable, chemically and physically, to be consistently dispensed in accurate metered doses, even after prolonged storage with potential temperature fluctuations of between 0° and 40° C. Accordingly, the active ingredient must be compatible with the excipients used in the formulation and should not aggregate in a manner which would result in a loss of accurate dose delivery, for example by precipitation from a liquid formulation or by caking of a powder formulation. To maximize retention of an intranasal formulation within the nasal passages of a patient after administration, particularly of a liquid formulation, it is desirable to deliver the unit dosage of active ingredient within a relatively small delivery volume, for example 50–200 μl, preferably about 100 μl. This may necessitate the use of high concentrations of medicament and highly soluble active ingredients are therefore advantageous. Clearly, an active ingredient must also be presented in a form which is readily absorbed through the nasal mucosa but which is unassociated with any adverse effects such as irritancy.

As indicated above, it has been found that for intranasal administration the salt according to the invention may advantageously be administered in the form of a solution.

Solutions will generally be aqueous; they may be prepared from water alone (for example sterile, pyrogen-free water), or from water and a pharmaceutically acceptable co-solvent (for example ethanol, propylene glycol, and polyethylene glycols such as PEG 400).

Such solutions may additionally contain other excipients such as preservatives (for example benzalkonium chloride and phenylethyl alcohol), buffering agents, tonicity-adjusting agents (for example sodium chloride), viscosity enhancing agents, absorption enhancers, flavouring agents (such as menthol, eucalyptol, camphor and methyl salicylate in amounts of from about 0.001 to about 0.5% w/w) and sweetening agents (for example saccharin or saccharin sodium in amounts of from about 0.01% w/w to about 10% w/w, preferably in the range of 0.01 to 2% w/w).

Preferably solutions according to the invention will be sterile and free from preservatives. Sterile formulations may be prepared by methods known in the art, for example by aseptic manufacture or sterilization of bulk products.

Solutions are applied directly to the nasal cavity by conventional means, for example with a dropper, pipette or spray. The formulations may be provided in single or multidose form. In the latter case a means of dose metering is desirably provided. In the case of a dropper or pipette this may be achieved by the patient administering an appropriate, predetermined volume of the solution. In the case of a spray this may be achieved for example by means of a metering atomizing spray pump.

Intranasal administration may also be achieved by means of an aerosol formulation in which the compound is provided in a pressurized pack with a suitable propellant such as a chlorofluorocarbon (CFC), for example dichlorodifluoromethane, trichlorofluoromethane or dichloro-tetrafluoroethane; a hydrofluorocarbon (HFC), for example 1,1,1,2-tetrafluoroethane or 1,1,1,2,3,3,3-heptafluoropropane; a hydrochlorofluorocarbon (HCFC), for example chlorodifluoromethane, 1,1,1-chloro-difluoroethane, 1,1-dichloro-2,2,2-trifluoroethane, 1-chloro-1,2,2,2-tetrafluoroethane or 1,1,1-dichlorofluoroethane; carbon dioxide; or other suitable gas. The dose of drug may be controlled by provision of a metered valve. Alternatively, a piezoelectric device may be employed in order to achieve the required spray.

Preferably a pharmaceutical composition adapted for intranasal administration which contains the salt according to the invention will be in the form of an aqueous solution.

Thus, the present invention also provides a substantially isotonic aqueous solution of the salt of Formula I as defined above; as well as the use of such a solution in the preparation of pharmaceutical compositions adapted for intranasal administration.

Aqueous solutions of the salt of the present invention adapted for intranasal administration will suitably have a pH in the range 4 to 9. Preferably the pH of aqueous solutions of the salt according to the invention for intranasal administration will be between 5 and 7. At a concentration of 160 mg/ml (expressed in terms of free base), the pH of an aqueous solution of the sulfate salt of Formula I above is found to be approximately 5.3–5.8. This is particularly advantageous, since such solutions require no substantial adjustment of pH prior to use. Solutions of more acidic salts, e.g., hydrochloride salt, with pH values falling outside the acceptable range, will require significant adjustment of the pH by the addition of further excipients, in particular substantial amounts of buffers, and this in turn will have a deleterious effect upon the pharmaceutical properties of the resulting solution owing to the concomitant increase in tonicity. Nevertheless, should adjustment of the pH of aqueous solutions of the salt of Formula I be required, this can conveniently be effected by conventional means, such as by the controlled addition of a pharmaceutically acceptable buffer, acid or base.

It will be appreciated that aqueous solutions of the bisulfate salt according to the invention may conveniently be prepared by dissolving the salt in water. Alternatively, such solutions may be obtained by mixing 1 molar equivalent of the free base: N,N-dimethyl-2-[5-(1,2,4-triazol-1-ylmethyl)-1H-indol-3-yl]ethylamine, with 1 molar equivalent of concentrated or dilute sulphuric acid, in water.

For intranasal administration, aqueous solutions of the salt in accordance with the present invention will ideally contain the salt at a concentration of 1 mg/ml to 200 mg/ml, more generally from 10 mg/ml to 190 mg/ml, and a very useful concentration of 160 mg/ml, all expressed in terms of the free base, N,N-dimethyl-2-[5-(1,2,4-triazol-1-ylmethyl)-1H-indol-3-yl]ethylamine.

For intranasal administration, the salt of the present invention may conveniently be presented in unit dose form. A convenient unit dose formulation for intranasal administration contains the active ingredient in an amount of from 0.1 mg to 100 mg, suitably in the range of 1 to 60 mg, preferably 2 to 40 mg, which may be administered to either one or both nostrils. Ideally, 1 mg to 35 mg of the active ingredient is administered in a single dose to one nostril.

A typical unit dose formulation may be provided as a single dose in a sealed unit, for example a vial of glass or plastics material which may be filled and sealed using conventional manufacturing techniques. Alternatively, a sealed vial of plastics material may be produced by form-fill-seal technology. Ideally the vial and the components of the pharmaceutical formulation filled therein are heat stable. The sealed vial may be sterilized, for example by autoclaving at 121° C. for not less than 15 minutes, or alternatively by gamma irradiation of the container followed by sterile filtration of the solution, to provide a sterile unit dosage vial which can be assembled into a convenient delivery device prior to use. Generally, the unit dose volume is 50 to 200 $\mu$l, for example 100 $\mu$l.

Devices for administering the intranasal formulation according to the invention include the single dose dispenser device described in U.S. Pat. No. 5,307,953; the Bespak multidose device, obtainable from Bespak, Kings Lynn, United Kingdom; and, the Valois "Monospray" single dose spray device as described in WO-A-93/00172.

According to a further aspect, the present invention provides a process for the preparation of the crystalline bisulfate salt of Formula I as defined above or a solvate thereof, which process comprises reacting the free base N,N-dimethyl-2-[5-(1,2,4-triazol-1-ylmethyl)-1H-indol-3-yl]ethylamine of structural Formula II below:

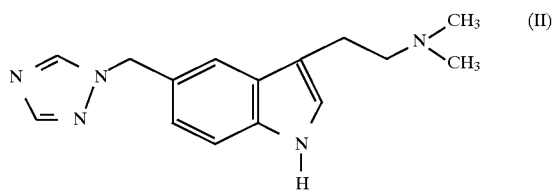

with approximately 1 molar equivalent of sulphuric acid in a suitable solvent system.

The process is carried out generally at about 0–5 degrees C., and usually at 0 degrees C.

The process can be conducted by slowly adding one molar equivalent of the sulfuric acid, in a concentration of about 1M–10M, to one molar equivalent of the free base dissolved in an organic solvent at 0–5 degrees C. Generally the organic solvent is, e.g., $C_1$–$C_4$ linear or branched alcohol, e.g., ethanol, isopropanol or methanol.

Alternatively, the process can be conducted by adding one molar equivalent of the free base dissolved in an organic solvent to one molar equivalent of the sulfuric acid in an aqueous organic solvent at about 0–5 degrees C.

The process is advantageously carried out after this initial mixing of reactants by stirring the resulting mixture at room temperature for about 30 minutes to an hour. The crystalline bisulfate is then isolated and purified by conventional procedures.

The crystalline bisulfate salt of Formula I above can also be prepared by salt exchange, which comprises treating a salt of the compound of Formula II above, other than the (1:1) bisulfate salt of Formula I, with a suitable bisulfate salt.

Examples of appropriate bisulfate salts which may be utilized in the above salt exchange procedure include metal bisulfates, such as sodium bisulfate or silver bisulfate, and sulfated ion exchange resins. The reaction is conveniently carried out in an aqueous medium.

The starting free base N,N-dimethyl-2-[5-(1,2,4-triazol-1-ylmethyl)-1H-indol-3-yl]ethylamine of structural Formula II can be prepared by the procedures which are disclosed in U.S. Pat. No. 5,298,520, hereby incorporated by reference for this particular purpose.

Hydrates of the crystalline bisulfate, e.g., mono- or dihydrate, can be obtained in conventional manner by exposing the crystalline bisulfate to a stream of humid air at room temperature for a period of time of about 4–24 hours.

Solvates, e.g., ethanolates, can also be formed in this manner, for example, by using an air stream saturated with ethanol vapor.

In a still further aspect, the present invention provides a method for the treatment and/or prevention of clinical conditions for which a selective agonist of 5-HT$_1$-like receptors is indicated, which method comprises administering to a patient in need of such treatment a therapeutically effective amount of the salt of Formula I as defined above or a pharmaceutically acceptable solvate thereof. In a particular embodiment of the method according to the invention, the salt of Formula I or its pharmaceutically acceptable solvate is administered in the form of a solution, preferably an aqueous solution adapted for intranasal administration.

The present invention also provides the use of the salt of Formula I as defined above or a pharmaceutically acceptable solvate thereof for the manufacture of a medicament, suitably a solution and preferably an aqueous solution adapted for intranasal administration, for the treatment and/or prevention of clinical conditions for which a selective agonist of 5-HT$_1$-like receptors is indicated.

The following non-limiting Examples are intended to illustrate the present invention and should not be construed as being limitations on the scope or spirit of the instant invention.

EXAMPLE 1

N,N-Dimethyl-2-[5-(1,2,4-triazol-1-ylmethyl)-1H-indol-3-yl]ethylamine bisulfate

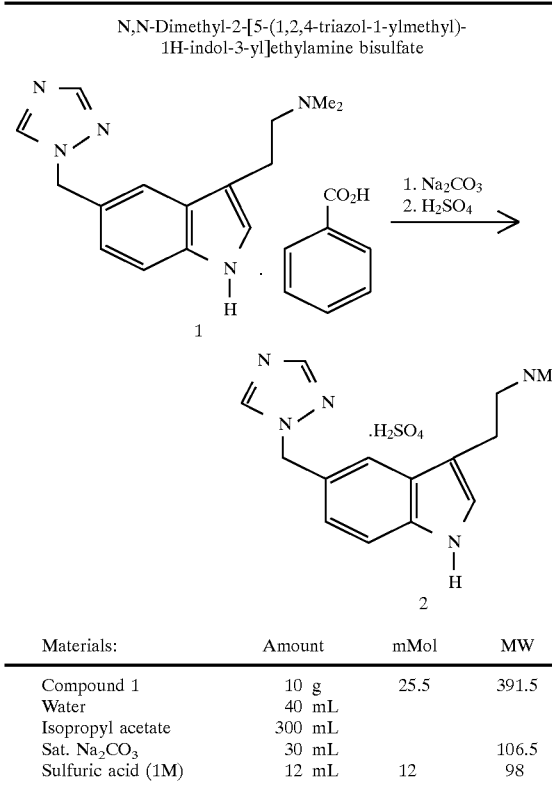

| Materials: | Amount | mMol | MW |
|---|---|---|---|
| Compound 1 | 10 g | 25.5 | 391.5 |
| Water | 40 mL | | |
| Isopropyl acetate | 300 mL | | |
| Sat. $Na_2CO_3$ | 30 mL | | 106.5 |
| Sulfuric acid (1M) | 12 mL | 12 | 98 |

To a mixture of water (40 mL) and isopropyl acetate (150 mL) at room temperature is added Compound 1. Saturated $Na_2CO_3$ (30 mL) is added portionwise, keeping the reaction temperature between 20°–25° C. The isopropyl acetate (IPAc) layer is separated. The aqueous layer is extracted with 150 mL of isopropyl acetate. The IPAc layers are combined, washed with 15 mL of water, and concentrated in vacuo to give the free base, N,N-dimethyl-2-[5-(1,2,4-triazol-1-ylmethyl)-1H-indol-3-yl]ethylamine of Compound 1, as a white solid.

EXAMPLE 2

To 3.20 g (11.89 mmol) of the above free base in 50 mL of EtOH at 0° C. is added sulfuric acid (1M, 12 mL) dropwise over 30 min, giving a clear solution. The solution is concentrated in vacuo to dryness and triturated with 20 mL of EtOH to give a white slurry. The solid is filtered, washed with 40 mL of EtOH and dried in oven (40° C. vacuum/nitrogen) to give Compound 2, N,N,-dimethyl-2-[5-(1,2,4-triazol-1-ylmethyl)-1H-indol-3-yl]ethylamine bisulfate, as a white crystalline solid (Thermogravimetric analysis showed 0.4% weight loss of volatiles upon heating, NaOH titration for sulfate showed: 29.9% $SO_4^=$, Ion chromatography assay for sulfate ion showed: 29.4% $SO_4^=$, theoretical calculation for $SO_4^=$: 26.7%).

EXAMPLE 3

To a sulfuric solution (conc. $H_2SO_4$, 1.43 g, 14.3 mmol) in a mixture of 5.0 mL of $H_2O$ and 5 mL of EtOH at 0° C. is added a solution of free base (3.5 g, 13 mmol) in 40 mL of EtOH over 30 min. A hazy solution is obtained. This mixture is seeded with the above Compound 2 (200 mg) and aged at 0° C. for 0.5 h to give a white slurry. The solid is filtered, washed with 40 mL of EtOH and dried in oven (40° C. vacuum/nitrogen) to give Compound 2 as a white crystalline solid.

The X-ray diffraction pattern of the crystalline bisulfate salt, Compound 2, is illustrated in FIG. 1.

The X-ray pattern was obtained on a Phillips APD 3720 apparatus, using Cu $K_\alpha$ radiation.

Figure 2:
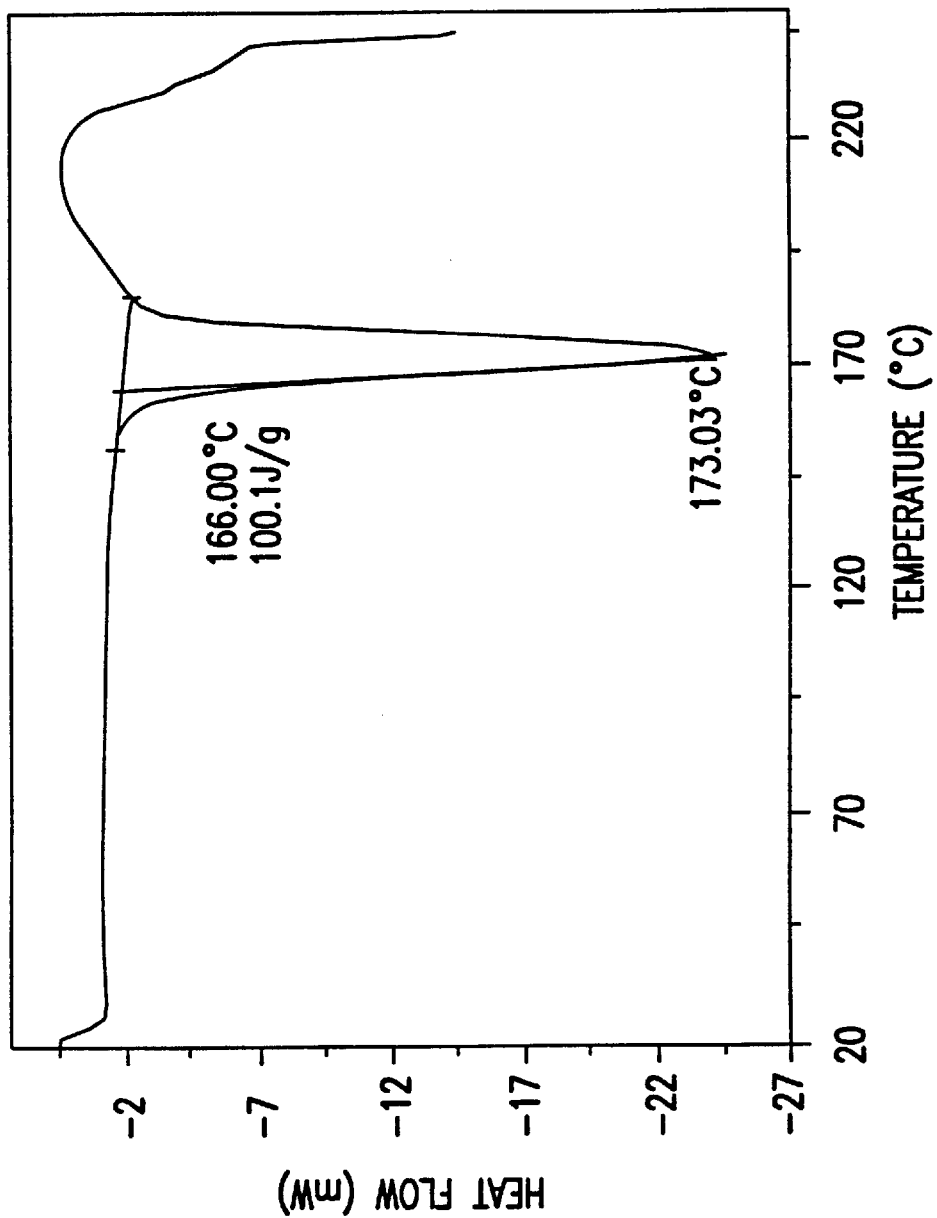
FIG. 2 is a differential scanning calorimeter (DSC) curve of the crystalline bisulfate compound of Formula I.

The differential scanning calorimeter (DSC) curve is illustrated in FIG. 2.

The DSC curve was taken on a TA 2100 apparatus with a heating rate of 10 degrees C./minute, under nitrogen atmosphere and in an open cup.

EXAMPLE 4

| Buffered sublingual tablet containing 50 µg (expressed as free base) of active ingredient Compound 2 | |
|---|---|
| Compound 2 | 0.068 mg |
| Avicel PH 200 | 91.194 mg |
| Starch 1500 | 22.0 mg |
| Sodium bicarbonate | 67.5 mg |
| Anhydrous sodium carbonate | 20.0 mg |
| Blue FD & C No. 2 Aluminium Lake | 0.55 mg |
| Saccharin sodium | 11.0 mg |
| Peppermint NAEFCO/P05.51 | 6.6 mg |
| Magnesium stearate | 1.1 mg |
| Total weight | 220.0 mg |

All the ingredients except magnesium stearate are mixed together in a suitable blender. The resulting mixture is then lubricated with magnesium stearate and compressed on a tablet press.

EXAMPLES 5 AND 6

| Sterile intranasal formulation | Example 5 | Example 6 |
|---|---|---|
| Compound 1 Free Base | 0.85 mg | 170 mg |
| Sulphuric Acid (concentrated) BP | 0.31 mg | 61.8 mg |
| Bulk Water for Injections QS | to 1 ml | to 1 ml |

The free base of Compound 1, N,N-dimethyl-2-[5-(1,2,4-triazol-1-ylmethyl)-1H-indol-3-yl]ethylamine, is dissolved in the sulphuric acid previously diluted with water. The solution is made up to volume.

The solution can be packaged for intranasal administration, for example by filling into vials, sealing and sterilizing the vials by autoclaving at 121° C. for not less than 15 minutes, or sterilized by filtration and aseptically transferred into sterile containers.

EXAMPLES 7 AND 8

| Preserved intranasal formulation | Example 7 | Example 8 |
|---|---|---|
| Compound 1 Free Base | 0.85 mg | 170 mg |
| Sulphuric Acid (concentrated) BP | 0.31 mg | 61.8 mg |
| Phenylethyl Alcohol USP | 4.0 mg | 4.0 mg |
| Benzalkonium Chloride USNF | 0.2 mg | 0.2 mg |
| Purified Water B. P. | to 1 ml | to 1 ml |

The free base of Compound 1 is dissolved in the sulphuric acid previously diluted with water. Phenylethyl alcohol and benzalkonium chloride are added and the solution made up to volume.

In a similar manner further preserved formulations are prepared containing 1, 5, 10, 50, 80, 100 and 150 mg/ml of Compound 2.

Formulations can be administered in unit dose volumes of 100 microliters to either one or both nostrils of patients suffering from a moderate or severe migraine attack to deliver a dose of 0.1, 1, 5, 10 or 17 mg of Compound 2.

EXAMPLES 9 AND 10

| Sterile intranasal formulation | | |
|---|---|---|
| | Example 9 | Example 10 |
| Compound 2 | 1 mg | 200 mg |
| Bulk Water for Injections QS | to 1 ml | to 1 ml |

Compound 2 of Formula (I) is dissolved in water and the solution made up to volume.

The solution can be packaged for intranasal administration, for example by filling into vials, sealing and sterilizing the vials by autoclaving at 121° C. for not less than 15 minutes, or sterilized by filtration and aseptically transferred into sterile containers.

EXAMPLES 11 AND 12

| Alternative preserved intranasal formulation | | |
|---|---|---|
| | Example 11 | Example 12 |
| Compound 2 | 1 mg | 200 mg |
| Benzethonium Chloride | 0.2 mg | 0.2 mg |
| Purified Water B. P. | to 1 ml | to 1 ml |

Compound 2 is dissolved in water. Benzethonium chloride is added and the solution made up to volume.

EXAMPLES 13 AND 14

| Sterile intranasal formulation | | |
|---|---|---|
| | Example 13 | Example 14 |
| Compound 1 Free Base | 160 mg | 160 mg |
| Sulphuric Acid (conc.) BP | 58.2 mg | 58.2 mg |
| Sodium Saccharin BP | 10 mg | 20 mg |
| Bulk Water for Injections QS | to 1 ml | to 1 ml |

The free base of Compound 1 is dissolved in the sulphuric acid previously diluted with water. The solution is made up to approximately 90% of volume and the saccharin dissolved therein and the solution finally made up to volume.

The formulations are filled into vials in 100 μl aliquots, the vials are sealed and are sterilized by autoclaving at 121° C. for not less than 15 minutes. Alternatively the solutions can be sterilized by filtration and filled aseptically into sterile vials.

The formulations are administered in unit dose volumes of 100 μl to a single nostril of patients suffering from a moderate or severe migraine attack to deliver an equivalent dose of 16 mg of Compound 2.

EXAMPLE 15

| Sterile intranasal formulation | |
|---|---|
| Compound 2 | 5.91 mg |
| Saccharin Sodium USP | 0.500 mg |
| Monobasic Potassium Phosphate NF | 0.834 mg |
| Dibasic Sodium Phosphate (Anhydrous) USP | 0.077 mg |
| Purified Water USP QS | to 0.1 ml |

Compound 2 is dissolved in the purified water together with the two phosphate buffers. The solution is made up to approximately 90% of volume and the saccharin dissolved therein and the solution finally made up to volume.

The formulation is filled into a vial in 100 μl aliquot, the vial is sealed and sterilized by autoclaving at 121° C. for not less than 15 minutes. Alternatively the solution can be sterilized by filtration and filled aseptically into a sterile vial.

The formulation is administered in a unit dose volumes of 100 μl to a single nostril of patients suffering from a moderate or severe migraine attack to deliver an equivalent dose of 5 mg of Compound 1 free base.

What is claimed is:

1. Crystalline N,N-dimethyl-2-[5-(1,2,4-triazol-1-ylmethyl)-1H-indol-3-yl]ethylamine bisulfate salt of structural Formula I:

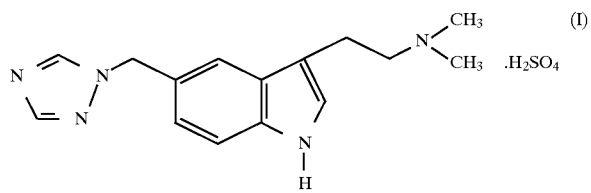

and pharmaceutically acceptable hydrate or ethanolate thereof.

2. A hydrate of the crystalline salt according to claim 1.

3. The crystalline salt of claim 1 characterized by the X-ray diffraction pattern of FIG. 1.

4. A crystalline salt comprising the ions of mono-protonated N,N-dimethyl-2-[5-(1,2,4-triazol-1-ylmethyl)-1H-indol-3-yl]ethylamine cation and bisulfate anion.

5. A pharmaceutical composition comprising an effective amount of the salt according to claim 1 or a pharmaceutically acceptable hydrate or ethanolate thereof in association with one or more pharmaceutically acceptable carriers.

6. A pharmaceutical composition in solid form adapted for sublingual administration, comprising an effective amount of the salt according to claim 1 a pharmaceutically acceptable hydrate or ethanolate thereof; one or more pharmaceutically acceptable buffering agents capable of imparting to the buccal cavity following administration a pH of at least 7.5; and one or more pharmaceutically acceptable excipients.

7. A pharmaceutical composition adapted for intranasal administration comprising an effective amount of the salt according to claim 1 or a pharmaceutically acceptable hydrate or ethanolate thereof in association with one or more pharmaceutically acceptable carriers.

8. A composition according to claim 7 which is presented in the form of an aqueous solution.

9. A composition according to claim 7 which is presented in the form of a solution in sterile, pyrogen-free water.

10. A composition according to claim 7 wherein the salt is at a concentration of 1 mg/ml to 200 mg/ml, expressed as the free base.

11. A composition according to claim 10 wherein the salt is at a concentration of 10 mg/ml to 190 mg/ml, expressed as the free base.

12. A composition according to claim 11 wherein the salt is at a concentration of approximately 160 mg/ml, expressed as the free base.

13. A composition according to claim 7 presented in unit dosage form and wherein the active ingredient is in an amount of from 0.1 mg to 110 mg, expressed as the free base.

14. A composition according to claim 13 wherein the unit dose volume is 50 to 200 µl.

15. A method for the treatment of migraine, cluster headache, chronic paroxysmal hemicrania, headache associated with vascular disorders, tension headache and pediatric migraine, which method comprises administering to a patient in need of such treatment an effective amount of the salt according to claim 1, or a pharmaceutically acceptable hydrate or ethanolate thereof.

16. A process for preparing the crystalline bisulfate of claim 1 comprising the step of contacting one molar equivalent of N,N-dimethyl-2-[5-(1,2,4-triazol-1-ylmethyl)-1H-indol-3-yl]ethylamine in an organic solvent with about a one molar equivalent of sulfuric acid at a temperature in the range of about 0–5 degrees C.

17. The process of claim 16 wherein said organic solvent is a $C_1$–$C_4$ linear or branched alkanol.

* * * * *